United States Patent [19]

Rauchfuss

[11] Patent Number: 5,792,474
[45] Date of Patent: Aug. 11, 1998

[54] PROCESS FOR THE PRODUCTION OF RETARDED PHARMACEUTICAL COMPOSITIONS

[75] Inventor: Roland Rauchfuss, Freiburg, Germany

[73] Assignee: Goedecke Aktiengesellschaft, Berlin, Germany

[21] Appl. No.: 362,592

[22] PCT Filed: May 21, 1993

[86] PCT No.: PCT/EP93/01289

§ 371 Date: Jun. 16, 1995

§ 102(e) Date: Jun. 16, 1995

[87] PCT Pub. No.: WO93/24110

PCT Pub. Date: Dec. 9, 1993

[30] Foreign Application Priority Data

May 22, 1992 [DE] Germany ................. 42 16 948.8

[51] Int. Cl.⁶ .................................................... A61K 9/14
[52] U.S. Cl. .................. 424/489; 242/470; 242/490; 242/449; 242/458; 242/491
[58] Field of Search ......................... 424/470, 489, 424/490, 488, 449, 452

[56] References Cited

U.S. PATENT DOCUMENTS

| | | | |
|---|---|---|---|
| 4,483,847 | 11/1984 | Augart | 424/22 |
| 4,540,602 | 9/1985 | Motoyama et al. | 424/34 |
| 5,518,730 | 5/1996 | Fuisz | 424/426 |

FOREIGN PATENT DOCUMENTS 204596  5/1986  European Pat. Off. ......... A61K 9/22

*Primary Examiner*—D. Gabrielle Phelan
*Assistant Examiner*—William E. Benston, Jr.
*Attorney, Agent, or Firm*—Michael J. Atkins

[57] ABSTRACT

According to the present invention, there is provided a continuous method for the production of retarded pharmaceutical compositions by an extrusion process. A mixture of an active material, a low and high melting lipid or lipoid components is introduced by means of an extruder screw conveyor into a preheated extruder and brought to a temperature which is at most about 4° C. above the melting temperature of the low melting component at a pressure of about 200 to about 600 kPa(N/m²). The mass is extruded through a nozzle plate with a nozzle diameter of about 1.2 to about 4 mm and subsequently cooled, and if desired, granulated.

15 Claims, 1 Drawing Sheet

PROCESS FOR THE PRODUCTION OF RETARDED PHARMACEUTICAL COMPOSITIONS

This application is a 371 of PCT/EP93/01289 filed May 21, 1993.

FIELD OF THE INVENTION

The present invention is concerned with a process for the production of pharmaceutical compositions with retarded liberation of active materials. More specifically, a mixture of an active material, and a low and high melting lipid or lipoid components are introduced by means of an extruder screw conveyor into a preheated extruder and brought to a temperature which is at most 4° C. above the melting temperature of the low melting component at a pressure of 200 to 600 kPa (N/m$^2$). The mass is extruded through a nozzle plate with a nozzle diameter of 1.2 to 4 mm and subsequently cooled and, if desired, granulated.

BACKGROUND

From EP0 043,254 is a known process for the production of pharmaceutical compositions with a retarded release of active materials which is based upon a selective melting process of at least two lipid or lipoid components which have a retarding action for pharmaceutically active materials mixed with these components. Retarded release, or a more commonly referred to as sustained release, concerns the timed control of the liberation of active materials from active-material containing compositions and especially from pharmaceutical compositions. Retarded release compositions, therefore, achieve a prolongation of the period of action and avoid too quick and/or too concentrated a release of the active materials in the compositions, and too high of peaks of the blood or tissue levels, which can lead to undesirable side effects.

The process is characterized in that (a) the active material is finely divided;

(b) the active material in finely divided form is mixed not only with a finely divided, high melting lipid or lipoid component but also with a finely divided, low melting lipid or lipoid component, the weight ratio of the two lipid or lipoid components thereby being in the range of from 1:5 to 5:1;

(c) the resulting mixture of active material and lipid or lipoid components is brought to a temperature which lies above the melting point of the low melting component but below the melting point of the high melting component, the active material and the high melting lipid or lipoid component thereby being uniformly dispersed in the molten low melting lipid or lipoid component;

(d) after the melting of the low melting component, the resulting mixture is allowed to cool below the melting point thereof; and (e) during the cooling or thereafter, the resulting mixture is granulated, the statements "low melting" and "high melting" thereby being used with reference to the relationship to one another without including any particular melting points.

Although it has already proved to be technically useful, the said process has certain disadvantages which, in particular, impede a continuous and automatically controlled production process. Thus, hitherto, it has not been possible to carry out the melting process continuously. In the Patent Specification, it is admittedly suggested, inter alia, to bring about the melting of the low melting component solely by means of the frictional heat of an extruder and, in this way, to omit a separate heating of the mixture. However, experiments recently carried out have shown that the frictional heat of an extrusion process is not sufficient completely to melt the low melting component. Therefore, the extrudate obtained is inhomogeneous and cannot be used for the granulation or other working up to give a medicament. Consequently, hitherto it has not been possible homogeneously to extrude the partly melted product. If, now, an attempt is made to increase the frictional heat by increasing the speed of rotation of the screw conveyor, then, without the working temperature increasing substantially, surprisingly a demixing takes place and, due to an extreme pressure increase in front of the nozzle plate, the extruder is sometimes stressed as far as a material destruction (breakage of the screw conveyor) without it having been possible to achieve the desired effect. Consequently, according to EP0 043,254, as previously, each batch must itself be mixed in appropriately dimensioned vessels, heated and again cooled within a previously determined period of time scheme. This is not only time-consuming but is automatically involved with many empty runs for cleaning and resupplying between the actual production batches. According to the previous production process in a 114 kg capacity planet mixer, the heating up time up to the melting range of 58° to 60° C. itself amounted, for example, to 1 hour. Furthermore, the material loss, i.e. the loss of active and adjuvant materials which remain adhering to the walls of the vessel and which, as a rule, are lost in the course of the cleaning process, is far from negligible. A further disadvantage of the process is that, after completion of the melting process, the final mixture is obtained in large lumps or as a melt cake which must first be removed from the melting vessel by manual shovelling and must then be comminuted before the final retarded mixture can be transferred to a granulator.

However, attempts to use an extruder with additional heating also initially failed completely. Even with the supply of heat, it was, namely, first not possible to produce an extrudate. Starting from the obvious assumption that the very short residence time of 2 to 5 minutes of the mixture in the extruder required a high melting temperature, as melting temperature there was chosen a temperature range lying only slightly below the melting point of the high melting component. As was to have been expected, the low melting component was thereby melted but, at the same time, an unexpected squeezing effect occurred which resulted in the low melting component being separated from the remainder of the mixture and being pressed in molten form through the nozzle plate. The mixture remaining in the extruder was thus separated from the "lubricant" and solidified. The frictional resistance thereby increased to such an extent that the extruder was stopped. Attempts to overcome this problem by a variation of the speed of rotation of the screw conveyor or by reducing the diameter of the nozzle were unsuccessful. A reduction of the temperature was not carried out since, due to this means, only a further impairment of the results was to have been expected. In the case of this consideration, it was, in particular, taken into account that a lower melting temperature would automatically undesirable prolong the period of residence of the mixture in the extruder but the deleterious squeezing out effect can, therefore, thereby not be favorably influenced because, upon reaching the nozzle plate, the whole of the low melting component must be present in a molten state and, consequently, under the pressure of from 200 to 600 kPA (N/m$^2$) prevailing in the extruder, would be squeezed off just as in the case of higher temperatures. Any kind of temperature influence on the squeezing off effect was not to have been expected. Furthermore, it was to have been expected that slow heating up and, consequently, low temperatures in the heating up phase would not only reduce the throughput but would also require a very long compression path and thus expensive apparatus.

It is an object of the present invention to overcome the above-mentioned disadvantages and to provide a fully automatic and continuously operating melting process according to EP-PS 0 043 254.

SUMMARY

Surprisingly, we have now found that, contrary to expectations and hitherto inexplicably, the harmful squeezing out effect in the case of a simple reduction of the working temperature into the lowest possible range disappears completely and that, consequently, the mixture known from and suggested in EP0 043,254, in spite of the many previously unsuccessful attempts, can, without special change of the composition and especially without any additions for the modification of the friction, be extruded to give extrudates which are outstandingly suitable for further working up when the well comminuted and pre-mixed powdered mass is subjected to an extrusion process at a temperature which lies at most about 4° C. above the melting temperature of the low melting lipid or lipoid component at a pressure of about 200 to about 600 kPa ($N/m^2$) and the partly melted and well mixed mass according to EP0 043,254 is extruded through a nozzle plate with a nozzle diameter of about 1.2 to about 4 mm.

DETAILED DESCRIPTION OF THE INVENTION

Figure 1:
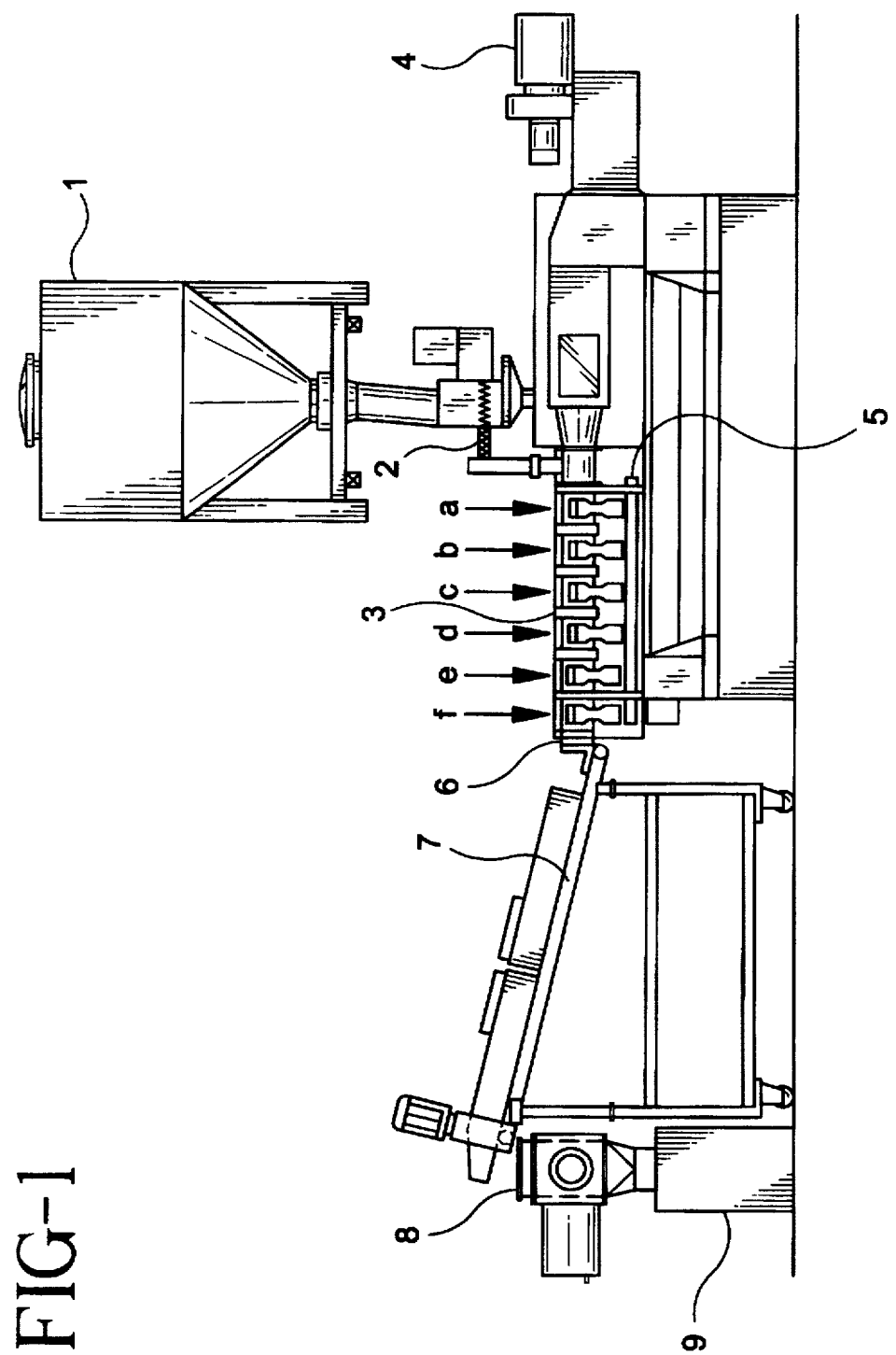
FIG. 1 is a cross-sectional elevation view of an extruder.

According to the present invention, the temperature in the extruder is to be not more than about 1° to about 4°, preferably about 1° to about 3° and most preferably only about 1° to about 2° C. above the melting temperature of the low melting component. Thus, the temperature of the heating mantle used must be correspondingly so adjusted that these temperature ranges are maintained in the mixture to be worked up over the whole length of the screw conveyor. Only shortly before passing the nozzle can the temperature be lowered to the region of the temperature of solidification of the low melting component when, by means of a sufficient speed of conveying, care is taken that this component can solidify only after passing the nozzle plate.

However, even when the temperature lies in the above-given optimum range, a usable, i.e. granulatable product which can be converted into a pharmaceutical is only obtained when, at the same time, the diameter of the nozzles is adjusted to a size adapted to the process. If the nozzle diameter is less than about 1 mm, then the nozzle plate becomes blocked up and the extruder is stopped by the increasing friction, which can result in considerable damage to the machine. If, on the other hand, the diameter is too great, i.e. greater than about 4 mm, then a product is obtained which admittedly appears to be usable but which, in actuality, is only melted on the surface. There is, as it were, obtained a tube with a melted-on wall and a powdered filling. Thus, here, too, it is important to find the correct diameter range. This is about 1.2 to about 4, preferably about 1.3 to about 3 and more preferably about 1.5 to about 2 mm.

The speed of rotation of the screw conveyor(s) is, corresponding to the extruder used and to the mixture to be worked up, to be so adjusted that the process pressure of about 200 to about 500 kPa ($N/m^2$) aimed for is achieved. A typical range of speed of rotation for an extruder with a screw conveyor length of about 1200 mm is, in the case of a melt pressure of about 200 to about 600 kPa ($N/m^2$), from about 50 to about 200 rpm.

In comparison with the process known from the above-mentioned prior art, the process according to the present invention possesses considerable advantage. Due to the continuous method of production, the finishing time for a unit amount can be considerably reduced. For example, for the production of 450 kg of granulate hitherto 16 working hours were needed. By means of the process according to the present invention, the same amount can be produced in only 4 working hours. The actual production time is thereby reduced by about 50%. The extruder requires less space and operates very economically. For example, with an extruder with a screw conveyor length of only 1400 mm, 110 to 130 kg of extrudate can be produced per hour.

The present invention will now be described in more detail with reference to the accompanying FIG. 1. The following examples are given for the purpose of illustrating the present invention, but are not meant in any way to restrict the effective scope of the invention.

EXAMPLES

From a storage container (1), a previously prepared, finely divided mixture consisting of:

37.5 kg hydrogenated castor oil, m.p. 80°–85° C.

60.0 kg powdered stearic acid, m.p. 55°–56° C.

90 kg diltiazem hydrochloride 255.5 kg lactose K 1.5 kg magnesium stearate 1.75 kg carboxymethylcellulose is passed via a dosing screw conveyor (2) to the actual extruder (3). The extruder (3) is divided up into several temperable sections (a–f) and is driven by a controllable motor (4). The mixture is conveyed through the extruder (3) preheated by the heatable mantle (5), at a speed of rotation of 170–180 r.p.m. The diameter of the screw conveyor is 50 mm. In all sections, the mantle temperature is 58°–60° C., which corresponds to a working temperature of 58°–60°. After an average period of residence of 2 to 4 minutes, the partly melted product is extruded through a nozzle plate (6). The nozzle plate (6) contains 20 nozzle openings each with an inner diameter of 1.5 to 3 mm. Under the described conditions, the apparatus conveys 110 to 120 kg of extrudate per hour. The extrudate is cooled substantially to ambient temperature in the form of fine, uniform strands on a slowly moving conveyor belt and is subsequently passed to a granulator (8). The final granulate finally reaches a collection container (9). In the simplest case, the sections (a) to (f) are uniformly tempered so that, in the case of passing through the extrusion process, the same working temperature prevails over the whole of the length of the screw conveyor (1400 mm). However, it is also possible initially to work at a somewhat higher temperature and gradually to decrease this until, possibly in the last section (f), the working temperature has been reduced almost to the solidification temperature of the low melting component. In this way, the cooling phase is shortened somewhat without it resulting in a blockage of the nozzles.

Otherwise, the mixtures described in EP0 043,254 can be used and working up without alteration.

A batch for the production of 120 mg diltiazem compositions contains, for example:

96 kg diltiazem hydrochloride
272 kg lactose K
40 kg hydrogenated castor oil
4.8 kg carboxymethylcellulose
65 kg stearic acid
1.6 kg magnesium stearate.

A batch for the production of 120 mg diltiazem compositions contains, for example:

120 kg diltiazem hydrochloride
215.3 kg lactose K
64 kg stearic acid NF
40 kg hydrogenated castor oil
2.25 kg carboxymethylcellulose
2.25 kg magnesium stearate.

A batch for the production of 180 mg diltiazem compositions contains, for example:

180 kg diltiazem hydrochloride
144.124 kg lactose K
48 kg hydrogenated castor oil
68.2 kg stearic acid NF
1.124 kg hydroxyethylcellulose
2.3 kg magnesium stearate.

A batch for the production of 240 mg diltiazem compositions contains, for example:

13.5 kg lactose X
24 kg diltiazem hydrochloride
12 kg hydrogenated castor oil
10 kg stearic acid
0.175 kg hydroxyethylcellulose
0.4 kg magnesium stearate.

A batch for the production of norfenefrine compositions contains, for example:

58.5 kg norfenefrine hydrochloride
152.1 kg lactose K
5.85 kg titanium dioxide
29.25 kg hydrogenated castor oil
43.876 kg stearic acid NF
2.924 kg carboxymethylcellulose.

A further batch for the production of norfenefrin compositions contains, for example:

30 kg norfenefrine hydrochloride
166 kg lactose X
6 kg titanium dioxide
30 kg hydrogenated castor oil
44 kg stearic acid NF
4 kg carboxymethylcellulose.

While there have been described what are presently believed to be the preferred embodiments of the invention, those skilled in the art will realize that changes and modifications may be made thereto without departing from the spirit of the invention, and it is intended to claim all such changes and modifications as fall within the true scope of the invention.

What is claimed is:

1. Process for the production of a pharmaceutical composition with retarded liberation of active material comprising the steps of:

(a) mixing the active material not only with a high melting lipid or lipoid component but also with a low melting lipid or lipoid component, the weight ratio of the two lipid or lipoid components being in the range of about 1:5 to about 5:1;

(b) introducing the resulting mixture by means of an extruded screw conveyor into a preheated extruded;

(c) bringing the resulting mixture of active material and lipid or lipoid components to a temperature which lies above the melting point of the low melting component but below the melting point of the high melting component, the temperature being at most 40 C above the melting temperature of the low melting component, the so heated mixture being subject to a pressure of about 200 to about 600 kPa($Nm^2$), the active material and the high melting component thereby being uniformly dispersed in the completely molten low melting component and extruded through a nozzle plate with a nozzle diameter of about 1.2 to about 4 mm;

(d) allowing the resulting mixture, after melting of the low melting component to cool to below the melting point thereof, and (e) granulating the resulting mixture during the cooling or thereafter.

2. Process according to claim 1 wherein the diameter of the screw conveyor is about 50 mm.

3. Process according to claim 1, wherein the temperature according to (d) is a working temperature of about 58° to about 60° C.

4. Process for the production of a pharmaceutical composition with retarded liberation of active material comprising the steps of:

(a) mixing the active material not only with a high melting lipid or lipoid component but also with a low melting lipid or lipoid component, the weight ratio of the two lipid or lipoid components being in the range of about 1:5 to about 5:1;

(b) introducing the resulting mixture by means of an extruder screw conveyor into a preheated extruder;

(c) bringing the resulting mixture of active material and lipid or lipoid components to a temperature which lies above the melting point of the low melting component but below the melting point of the high melting component, the temperature being about 1 to about 30 C above the melting temperature of the low melting component, the so heated mixture being subjected to a pressure of about 200 to about 600 kPa ($N/m^2$), the active material and the high melting component thereby being uniformly dispersed in the completely molten low melting and extruded through a nozzle plate with a nozzle diameter of about 1.3 to about 3 mm;

(d) allowing the resulting mixture, after melting of the low melting component to cool to below the melting point thereof; and (e) granulating the resulting mixture during the cooling or thereafter.

5. Process according to claim 4, wherein the temperature according to (d) is about 1° to about 2° C. above the melting temperature of the low melting lipid or lipoid component.

6. Process according to claim 4, wherein the nozzle diameter in the nozzle plates is about 1.5 to about 2 mm.

7. Process according to claim 4, wherein the speed of rotation for the extruder is in the range from about 170 to about 180 rpm.

8. Process according to claim 4, wherein the screw conveyor length is about 1200 mm.

9. Process according to claim 4, wherein the diameter of the screw conveyor is about 50 mm.

10. Process according to claim 4, wherein the temperature according to (d) is a working temperature of about 58° to about 60° C.

11. Process for the production of a pharmaceutical composition with retarded liberation of active material comprising the steps of:

(a) mixing the active material not only with a high melting lipid or lipoid component but also with a low melting lipid or lipoid component, the weight ratio of the two lipid or lipoid components being in the range of about 1:5 to about 5:1;

(b) introducing the resulting mixture by means of an extruder screw conveyor into a preheated extruder;

(c) bringing the resulting mixture of active material and lipid or lipoid components to a temperature which lies above the melting point of the low melting component but below the melting point of the high melting component, the temperature being at most about 1 to about 20 C above the melting temperature of the low melting component, the so heated mixture being subjected to a pressure of about 200 to about 600 kPa ($N/m^2$), the active material and the high melting component thereby being uniformly dispersed in the completely molten low melting and extruded through a nozzle plate with a nozzle diameter of 1.5 to 2 mm;

(d) allowing the resulting mixture, after melting of the low melting component to cool to below the melting point thereof; and (e) granulating the resulting mixture during the cooling or thereafter.

12. Process according to claim 11, wherein the speed of rotation for the extruder is in the range from about 170 to about 180 rpm.

13. Process according to claim 12, wherein the screw conveyor length is about 1200 mm.

14. Process according to claim 13, wherein the diameter of the screw conveyor is about 50 mm.

15. Process according to claim 14, wherein the temperature according to (d) is a working temperature of about 58° to about 60° C.

* * * * *